(12) United States Patent
Bar-Or

(10) Patent No.: US 9,034,878 B2
(45) Date of Patent: May 19, 2015

(54) TREATMENT OF DISEASES

(71) Applicant: Ampio Pharmaceuticals, Inc., Englewood, CO (US)

(72) Inventor: David Bar-Or, Englewood, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

(21) Appl. No.: 13/940,374

(22) Filed: Jul. 12, 2013

(65) Prior Publication Data

US 2013/0303463 A1 Nov. 14, 2013

Related U.S. Application Data

(62) Division of application No. 13/227,109, filed on Sep. 7, 2011, now Pat. No. 8,507,496.

(60) Provisional application No. 61/512,151, filed on Jul. 27, 2011, provisional application No. 61/380,426, filed on Sep. 7, 2010.

(51) Int. Cl.
| | |
|---|---|
| *A61K 31/497* | (2006.01) |
| *A61K 31/4965* | (2006.01) |
| *A61K 38/12* | (2006.01) |
| *A61K 38/05* | (2006.01) |
| *A61K 31/495* | (2006.01) |
| *A61K 31/496* | (2006.01) |

(52) U.S. Cl.
CPC .............. *A61K 38/12* (2013.01); *Y10T 428/13* (2015.01); *A61K 38/05* (2013.01); *A61K 31/495* (2013.01); *A61K 31/496* (2013.01)

(58) Field of Classification Search
None
See application file for complete search history.

(56) References Cited

U.S. PATENT DOCUMENTS

| | | |
|---|---|---|
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,578,323 A | 11/1996 | Milstein et al. |
| 5,589,501 A | 12/1996 | Carrera et al. |
| 5,648,486 A | 7/1997 | Cai et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |

(Continued)

FOREIGN PATENT DOCUMENTS

| | | |
|---|---|---|
| CS | 254868 | 6/1987 |
| CZ | 2827.94 | 4/1996 |

(Continued)

OTHER PUBLICATIONS

"Diabetic Retinopathy—What you should know," National Institutes of Health, 2003, NIH Publication No. 06-2171, 24 pages.
Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.
Costa et al., "Aggregation of features of the metabolic syndrome is associated with increased prevalence of chronic complications in Type 2 diabetes," Diabetic Medicine, 2004, vol. 21, Iss. 3, 252-255.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Ramírez et al., "Platelet Activating Factor Modulates Microvascular Permeability through Nitric Oxide Synthesis," Microvascular Research, 1995, vol. 50, Iss. 2, pp. 223-234.

(Continued)

*Primary Examiner* — Jeffrey S Lundgren
*Assistant Examiner* — Stephanie Springer
(74) *Attorney, Agent, or Firm* — Sheridan Ross P.C.

(57) ABSTRACT

The invention provides (i) a method of treating metabolic syndrome in an animal, (ii) a method of suppressing the appetite of an animal, (iii) a method of treating obesity in an animal, (iv) a method of reducing the weight of an animal in need thereof, (v) a method of reducing a blood lipid level in an animal in need thereof, (vi) a method of treating non-alcoholic steatohepatitis in an animal, and (vii) a method of inhibiting adipogenesis. The methods comprise administering an effective amount of an active ingredient, wherein the active ingredient comprises a diketopiperazine, a prodrug of a diketopiperazine or a pharmaceutically-acceptable salt of either of them to the animal. The invention also provides a kit comprising a container holding a diketopiperazine, a prodrug of a diketopiperazine or a pharmaceutically-acceptable salt of either of them; and instructions for administration. The diketopiperazines have the formula given in the application.

3 Claims, 1 Drawing Sheet

(56) References Cited

U.S. PATENT DOCUMENTS

| | | |
|---|---|---|
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,217,047 B2 | 7/2012 | Bar-Or |
| 8,268,830 B2 | 9/2012 | Bar-Or et al. |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goddey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2010/0120056 A1 | 5/2010 | Bar-Or et al. |
| 2010/0144611 A1 | 6/2010 | Bar-Or et al. |
| 2010/0190696 A1 | 7/2010 | Bar-Or et al. |
| 2012/0022081 A1 | 1/2012 | Bar-Or et al. |
| 2012/0058934 A1 | 3/2012 | Bar-Or |
| 2012/0094918 A1 | 4/2012 | Bar-Or et al. |
| 2012/0157473 A1 | 6/2012 | Bar-Or |
| 2013/0090292 A1 | 4/2013 | Bar-Or et al. |
| 2014/0256642 A1 | 9/2014 | Bar-Or et al. |
| 2014/0286913 A1 | 9/2014 | Bar-Or et al. |
| 2014/0294738 A1 | 10/2014 | Bar-Or |
| 2014/0302114 A1 | 10/2014 | Bar-Or |

FOREIGN PATENT DOCUMENTS

| | | |
|---|---|---|
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | 57-32272 | 2/1982 |
| JP | 59-73574 | 4/1984 |
| JP | 61-112060 | 5/1986 |
| JP | 62-036331 | 2/1987 |
| JP | 63-290868 | 11/1988 |
| JP | 01-013075 | 1/1989 |
| JP | 3176478 | 7/1991 |
| JP | 05-163148 | 6/1993 |
| JP | 07-247474 | 9/1995 |
| JP | 08-277203 | 10/1996 |
| JP | 10-226615 | 8/1998 |
| JP | 10-245315 | 9/1998 |
| JP | 11-504509 | 4/1999 |
| JP | 2000-327575 | 11/2000 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |

(56) References Cited

FOREIGN PATENT DOCUMENTS

| WO | WO 00/20454 | 4/2000 |
|---|---|---|
| WO | WO 00/20840 | 4/2000 |
| WO | WO 00/22439 | 4/2000 |
| WO | WO 00/43000 | 7/2000 |
| WO | WO 00/57187 | 9/2000 |
| WO | WO 01/34586 | 5/2001 |
| WO | WO 01/91713 | 12/2001 |
| WO | WO 02/11676 | 2/2002 |
| WO | WO 02/12201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/034060 | 4/2004 |
| WO | WO 2004/048345 | 6/2004 |
| WO | WO 2004/054498 | 7/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |

OTHER PUBLICATIONS

Official Action for Canadian Patent Application No. 2,810,844 dated Jan. 14, 2014, 4 pages.
Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Hollyfield et al., "Oxidative damage-induced inflammation initiates age-related macular degeneration," Nature Medicine, 2008, vol. 14, No. 2, pp. 194-198.
Kullenberg et al., "Intraarticular Corticosteroid Injection: Pain Relief in Osteoarthritis of the Hip?," Journal of Rheumatology, 2004, vol. 31, No. 11, pp. 2265-2268.
Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.
Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.
"CENTRICON Centrifugal Filter Devices User Guide," Millipore Corp., Mar. 2005, 23 pages.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; Class B03, AN 1998-515050 XP002369751 & JP 10 226615 A (Pola Chem Ind Inc) Aug. 25, 1998.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of Immunology, Fourth Edition, Edited by Herbert et al., 1995, pp. 51-52 and 69.
"Tryprostatin A, *Aspergillus fumigates*," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from *Streptomyces griseus*," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).

(56) References Cited

OTHER PUBLICATIONS

Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al. "Commercial human albumin preparations for clinical use are immunosuppressive in vitro," Critical Care Medicine, Jun. 2006, vol. 34, No. 6, pp. 1707-1712.
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berman et al., "Psoriasis," PubMed Health, reviewed Nov. 22, 2011, available at www.ncbi.nlm.nih.gov/pubmedhealth/PMH0001470/?report=printable.
Berry et al., "Inhibition of Tau Polymerization by its Carboxy-Terminal Caspase Cleavage Fragment," Biochemistry, 2003, vol. 42, pp. 8325-8331.
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.
Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Brauns et al., "Selected cyclic dipeptides inhibit cancer cell growth and induce apoptosis in HT-29 colon cancer cells," Anticancer Research, 2004, vol. 24, pp. 1713-1720.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chan et al., "Site-Specific N-Terminal Auto-Degradation of Human Serum Albumin," Eur. J. Biochem., 1995, vol. 227, pp. 524-528.
Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of *Gymnoascus reessii*," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by *Aspergillus fumigatus* II. Physico-chemical properties and Structures," The Journal of Antibiotics, Jun. 1996, pp. 534-540.
D'Alagni et al. "Effect of Urea on the Optical Rotatory Dispersion of Diketopiperazines of l-Serine, l-Alanine, l-Lysine, l-Valine, and l-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.
Degrassi et al., "Plant Growth-Promoting *Pseudomonas putida* WCS358 Produces and Secretes Four Cyclic Dipeptides: Cross-Talk with Quorum Sensing Bacterial Sensors," Current Microbiology, 2002, vol. 45, pp. 250-254.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Esposito et al., "The Solution Structure of the C-Terminal Segment of Tau Protein," Journal of Peptide Science, 2000, vol. 6, pp. 550-559.

(56) References Cited

OTHER PUBLICATIONS

Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Fdhila et al., "dd-diketopiperazines: antibiotics active against *Vibrio anguillarum* isolated form marine bacteria associated with cultures of *Pecten maximus*" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).

Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.
Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from *Pseudomonas aeruginosa* and other Gram-negative bacteria," Moleclur Microbiology, 1999, vol. 33(6), pp. 1254-1266.
Hong et al., "Inhibitory effect against Akt of cyclic dipeptides isolated from *Bacillus* sp" J. Microbiol. Biotechnol., 18, 682-685 (2008).
Houston et al., "The cyclic dipeptide CI-4 [cyclo-(l-Arg-d-Pro)] inhibits family 18 chitinases by structural mimicry of a reaction intermediate," Biochem J., Nov. 15, 2002, vol. 368(Pt 1) (Abstract Only Provided).
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed-PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.
Ishii, et al. "Incidence of brain tumors in rats fed aspartame," Toxicology Letters, 1981, vol. 7, pp. 433-437.

(56) References Cited

OTHER PUBLICATIONS

Iyer et al. "Inflammatory lipid mediators in adipocyte function and obesity." Nature Reviews Endocrinology, Feb. 2010, vol. 6, pp. 71-82.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor of pituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al., "AKT signaling in regulating angiogenesis," Current Cancer Drug Targets, 2008, vol. 8, pp. 19-26.
Jiang et al. "Asymmetric Reformastky reaction catalyzed by amino acid derivatives," Huaxue Tongbao CKNI, 2001, vol. 10, pp. 637-640 (English Abstract).
Jicha et al., "Sequence Requirements for Formation of Conformational Variants of Tau Similar to Those Found in Alzheimer's Disease," Journal of Neuroscience Research, 1999, vol. 55, pp. 713-723.
Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.
Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).
Kasperska-Zajac et al. "Platelet Activating Factor as a Mediator and Therapeutic Approach in Bronchial Asthma." Inflammation, Apr. 2008, vol. 31, No. 2, pp. 112-120.
Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).
Kilian et al., "Biological activity of selected tyrosine-containing 2,5-diketopiperazines," Pharmazie, Apr. 2005, vol. 60(4), pp. 305-309 (Abstract Only Provided).
Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).
Kobayashi et al., "Neuropeptide Y and histidyl-proline diketopiperazine," Rinsho-Kensa, Japan, Sep. 1987, vol. 21, No. 9, pp. 984-991.
Kopple et al. "Conformation of Cyclo-(I-Threonine)2 and Cyclo-(I-Allo Threonine)2 : A Proton and Carbon N.m.r. Study." International Journal of Peptide Protein Research, Jul. 1981, vol. 18, No. 1, pp. 33-40.
Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).
Kow et al., "The Effects of the TRH Metabolite Cyclo(His-Pro) and Its Analogs on Feeding," Pharmacology, Biochemistry & Behavior, 1991, vol. 38, pp. 359-364.
Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.
Kulikov et al., "Review: The Bioregulatory Role of Platelet-Activating Factor in Intracellular Processes and Cell-Cell Interactions," 1997, www.protein.bio.msu.su/biokhimiya/contents/v63/full1/63010057.html, pp. 1-13.
Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).
Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).
Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).
Lechin et al., "Plasma Neurotransmitters and Cortisol in Chronic Illness: Role of Stress," J Medicine, 1994, vol. 25(3-4), pp. 181-192 (Abstract Only Provided).
Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).
Lee et al., "Characterization of an Elastase Inhibitor Produced by *Streptomyces lavendulae* SMF11," Journal of Microbiology and Biotechnology, 2000, vol. 10, No. 1, pp. 81-85.
Lee et al., "Cyclo (Leu-Gly attenuates the striatal dopaminergic supersensitivity induced by chronic morphine," Alcohol Drugs Res, 1987, vol. 7(1) (Abstract Only Provided).
Lehninger et al., "Amino Acids and Peptides," Chapter 5 of Principles of Biochemistry, 1993, 2nd edition, pp. 111-133.
Lindner et al., "[Effects of cyclic adenosine-3',5'-monophosphate and cyclo{Lys-Pro}.HCI neuronotrophic factors in tissue culture]," J Hirnforsch, 1987, vol. 28(3) (Abstract Only Provided).
Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).
Luca et al., "Determination of serotonin content and ceruloplasmin activity, of blood and CSF amino acid level in multiple sclerosis," Neurol Psychiatr (Bucur), 1986, vol. 24(3), pp. 153-159.
Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).
Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.
Mazza et al., "Potential energy calculations on phenylalanine rotamers in different boat forms of proline-containing cyclic dipeptides," Int. J. Pept. Protein Res., vol. 31, Feb. 1988, pp. 157-163.
McCain et al., "Endorphinergic modulation of immune function: potent action of the dipeptide glycyl-L-glutamine," Life Science, 1987, vol. 41, pp. 169-176.
McCain et al., "Modulation of Human T-Cell Suppressor Activity by Beta Endorphin and Glycyl-L-Glutamine," Int. J. Immunopharmoc, 1986, vol. 8(4), pp. 443-446.
McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.
Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.
Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).
Mesh, "Autoimmune Diseases," internet document www.ncbi.nlm.nih.gov/sites/entrez, accessed Oct. 31, 2007, 2 pages.
Michell et al., "Biomarkers and Parkinson's Disease," Brain, Aug. 2004, vol. 127, pp. 1693-1705.
Miller et al., "Peptide Inhibitor of Interleukin-8 (IL-8) Reduces Staphylococcal Enterotoxin-A (SES) Induced Neutrophil Trafficking to the Lung," Inflamm. Res., 1996, vol. 45, pp. 393-397.

(56) References Cited

OTHER PUBLICATIONS

Milne, et al. "The biological activity of selected cyclic dipeptides," J. Pharm. Pharmacol., 1998, vol. 50, pp. 1331-1337.
Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.
Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).
Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.
Mizuma et al., "Intestinal Absorption of Stable Cyclic Glycylphenylalanine: Comparison with the Linear Form," J. Pharm. Pharmacol., 1997, vol. 49, pp. 1067-1071.
Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).
Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).
Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.
Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).
Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).
Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.
Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).
Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.
Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).
Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).
Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).
Morley et al., "Neuropeptides and appetite: contribution of neuropharmacological modeling," Fed. Proc., Nov. 1984, vol. 43(14), pp. 2903-2907 (Abstract Only Provided).
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Moss et al. "Th1/Th2 cells in inflammatory disease states: therapeutic implications," Expert Opinion on Biological Therapy, Dec. 2004, vol. 4, No. 12, pp. 1887-1896.
Murray et al., "Role of α-Synuclein Carboxy-Terminus on Fibril Formation in Vitro," Biochemistry, 2003, vol. 42, pp. 8530-8540.
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
Nicholson et al., "NPI-2358 is a tubulin-depolymerizing agent: invitro evidence for activity as a tumor vascular-disrupting agent," Anticancer Drugs, Jan. 2006, vol. 17(1), pp. 25-31 (Abstract Only Provided).
Nitecki et al., "A Simple Route to Sterically Pure Kiketopiperazines" J. Org. Chem., 1968, vol. 33(2), pp. 864-866.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).
Pekary et al., "In vitro Production of a TRH-Homologous Peptide and His-Pro Diketopiperazine by Human Semen," J Androl, 1985, vol. 6(6), pp. 379-385 (Abstract Only Provided).
Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).
Prakash et al., "Synthesis and Biological Activity of Novel Neuroprotective Diketopiperazines," Bioorganic & Medicinal Chemistry, Sep. 2002, vol. 10(9), pp. 3043-3048.
Prasad, "Bioactive Cyclic Dipeptides," Peptides, 1995, vol. 16(1), pp. 151-164.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-1587.
Purves et al., Life: the Science of Biology, 3rd Ed. (1992), p. 376.
Purves et al. (Eds), Neuroscience, 2001, Sinauer Associates, Inc., 2nd Edition, pp. 75, 367, 400 and 403.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.

(56) References Cited

OTHER PUBLICATIONS

Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackling the missing elements," Neurol. Sci., Dec. 2005, vol. 26 Suppl. 4, pp. S215-S217.
Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, -β, and -γ on Interleukin-8 Gene Expression by Human Gingival Fibroblasts in Culture Upon Stimulation with Lipopolysaccharide from *Prevotella intermedia*, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al. "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan 1984, vol. 34(1) (Abstract Only Provided).
Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).
Schlingemann et al., "Role of vascular permeability factor/vascular endothelial growth factor in eye disease," Brit. J. Ophthalmology, vol. 81, 1997, pp. 501-512.
Sepetov et al., "Rearrangement, Racemization and Decomposition of Peptides in Aqueous Solution," Peptide Research, 1991, vol. 4(5), pp. 308-313 (Abstract Only Provided).
Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).
Shaw et al., "Future of early detection of lung cancer: the role of mouse models." Clin Cancer Res., Jul. 1; 11(13 Pt 2): 4999s-5003s, 2005.
Shimazaki et al., "Diketopiperazine Derivatives, a New Series of Platelet-Activating Factor Inhibitors," Chem. Pharm. Bull., 1987, vol. 35(8), pp. 3527-3530.
Shimazaki et al., "Diketopiperazines as a New Class of Platelet-Activating Factor Inhibitors," J. Med. Chem., 1987, vol. 30, pp. 1706-1709.
Shimazaki et al., "PAF Inhibitory Activity of Diketopiperazines: Structure-Activity Relationships," Lipids, 1991, vol. 26(12), pp. 1175-1178.
Shimi et al., "Isolation of Cairomycins A and C," Antimicrobial Agents and Chemotherapy, Jun. 1981, vol. 19(6), pp. 941-944.

Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).
Skates et al., "Molecular markers for early detection of renal carcinoma: investigative approach," Clin Cancer Res, Sep. 2004, vol. 10(18 Pt 2), pp. 6296S-6301S.
Smith et al., "Lesson 10, vol. 12—Asthma: Evolving Anti-Inflammatory Therapy," www.chestnet.org/education/pccu/vol12/lesson10.html, pp. 1-8, printed Jul. 20, 2000.
Smith et al., "Recent developments in drug therapy for multiple sclerosis," Mult. Soler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Sollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "*Lactobacillus plantarum* MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suzuki et al., "Effect of cyclic dipeptides containing histidine on pentobarbital narcosis," J. Pharm. Dyn., May 1981, vol. 4(5), pp. 377-379.
Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
't Hart et al., "Evaluating the validity of animal models for research into therapies for immune-based disorders," DDT, 2004, vol. 9(12), pp. 517-524.
Tascioglu et al., "Efficacy of intra-articular sodium hyaluronate in the treatment of knee osteoarthritis," Clinical Rheumatology, 2003, vol. 22, Iss. 2, pp. 112-117.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Varughese et al., "Crystal structure and conformation of cyclo-L-cystine," Int. J. Pept. Protein Res., vol. 18, Jul. 1981, pp. 88-102.

(56) References Cited

OTHER PUBLICATIONS

Vogel et al., "Disseminated tumor cells—Their detection and significance for prognosis of gastrointestinal and pancreatic carcinomas," Virchows Arch, 2001, vol. 439, pp. 109-117.

Walter et al., "Neurohypophyseal hormones, analogs, and fragments: their effect on puromycin-induced amnesia," Proc. Natl. Acad. Sci., Oct. 1975, vol. 72(10), pp. 4180-4184.

Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.

Wang et al., "A facile pathway to synthesize diketopiperazine derivatives," Tetrahedron Lett, 2002, vol. 43, pp. 865-867.

Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).

Weng et al., " Novel CCK-B receptor agonists: diketopiperazine analogues derived for CCK4 bioactive conformation," Regul Pept, Aug. 1996; vol. 65(1) (Abstract Only Provided).

Wennemers et al., "Diketopiperazine Receptors: A Novel Class of Highly Selective Receptors for Binding Small Peptides," Chem. Eur. J., 2001, vol. 7, No. 15, pp. 3342-3347.

Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.

Wilber et al., "Histidyl-proline diketopiperazine: a potent and chronic appetite-inhibiting neuropeptide," Trans Assoc. Am Physicians, 1986, vol. 99, pp. 245-249.

Wilkes et al. "Patient Survival after Human Albumin Administration: A Meta-Analysis of Randomized, Controlled Trials." Annals of Internal Medicine, Aug. 2001, vol. 135, No. 3, pp. 149-164.

Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).

Woehlecke et al., "Reversal of breast cancer resistance protein-mediated drug resistance by tryprostatin A.," Int J Cancer; Dec. 2003, vol. 107(5) (Abstract Only Provided).

Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).

Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.

Wyatt et al., "2,5-Diketopiperazines as potent and selective oxytocin antagonists 1: Identification, stereochemistry and initial SAR," Bioorg Med Chem Lett., May 16 2005, vol. 15(10), pp. 2579-2582 (Abstract Only Provided) PMID: 15863320.

Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).

Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).

Yang et al. "Increased hepatic platelet activating factor (PAF) and PAF receptors in carbon tetrachloride induced liver cirrhosis." Gut, Jan. 2004, vol. 53, No. 6, pp. 877-883.

Yi Es, "Hypersensitivity pneumonitis," Crit Rev Clin Lab Sci., Nov. 2002, vol. 39(6), pp. 581-629.

Yoshida et al., "PAF Inhibitors of Microbial Origin," Prog. Biochem. Pharmacol., 1988, vol. 22, pp. 68-80.

Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).

Zeng et al., "Synthesis of a small library of diketopiperazines as potential inhibitors of calpain," Bioorg Med Chem Lett, Jun. 2005, vol. 15(12), pp. 3034-3038.

Zieve, "Multiple sclerosis," PubMed Health, reviewed Sep. 26, 2011, available at www.ncbi.nlm.nih.gov/pubmedhealth/PMH0001747/?report=printable, 10 pages.

International Search Report for International (PCT) Patent Application No. PCT/US11/50618, mailed Feb. 23, 2012 5 pages.

Written Opinion for International (PCT) Patent Application No. PCT/US11/50618, mailed Feb. 23, 2012 7 pages.

International Preliminary Report on Patentability for International (PCT) Patent Application No. PCT/US11/50618, mailed Mar. 21, 2013, 9 pages.

Morely et al., "Histidyl-proline diketopiperazine decreases food intake in rats," Brain Research, 1981, vol. 210, Iss. 1-2, pp. 475-478.

Extended European Search Report for European Patent Application No. 11824041.5 dated Sep. 23, 2013, 6 pages.

Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.

Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.

Zander et al., "Allogeneic bone marrow transplantation for acute leukemia refractory to induction chemotherapy," Cancer, 1985, vol. 56, Iss. 6, pp. 1374-1379.

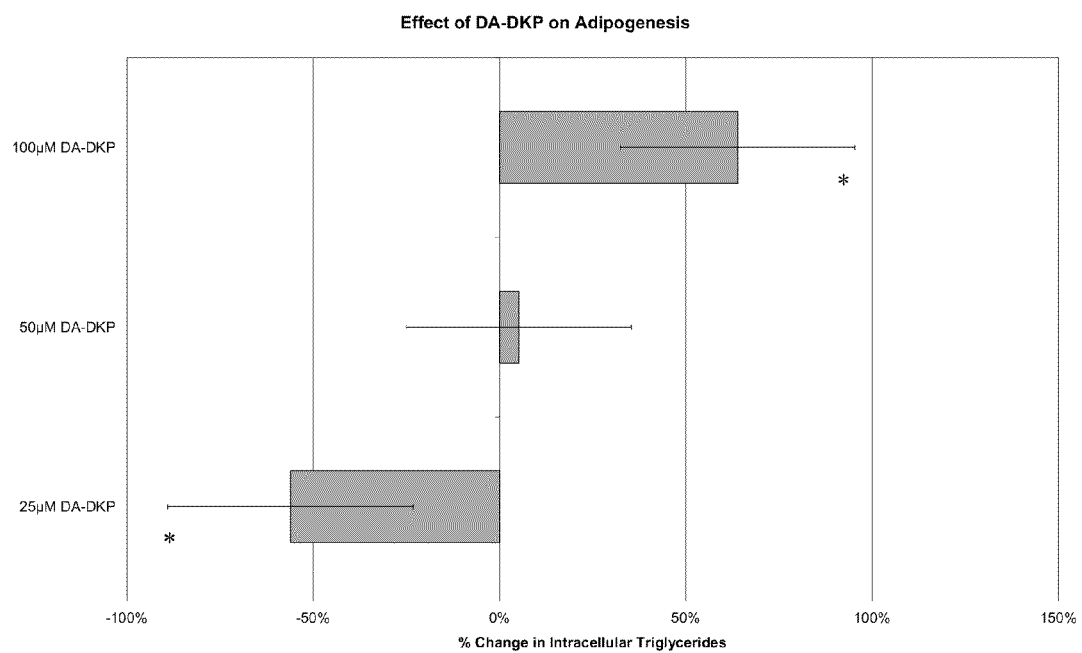

TREATMENT OF DISEASES

CROSS REFERENCE TO RELATED APPLICATIONS

The present application is a divisional application of U.S. patent application Ser. No. 13/227,109, filed Sep. 7, 2011, which claims the benefit of U.S. Provisional Patent Application Ser. No. 61/512,151, filed Jul. 27, 2011, and U.S. Provisional Patent Application Ser. No. 61/380,426, filed Sep. 7, 2010, the complete disclosures of which are incorporated herein by reference.

FIELD OF THE INVENTION

The invention relates to a treatment for metabolic syndrome comprising administering to an animal in need thereof an effective amount of a diketopiperazine of formula I set forth below, a prodrug of a diketopiperazine of formula I or a pharmaceutically-acceptable salt of either of them. The invention further relates to a method of suppressing the appetite of an animal, a method of treating obesity in an animal, a method of reducing the weight of an animal in need thereof, a method of reducing a blood lipid level in an animal in need thereof, a method of treating non-alcoholic steatohepatitis in an animal, and a method of inhibiting adipogenesis in an animal. These methods also comprise administering an effective amount of a diketopiperazine of formula I, a prodrug of a diketopiperazine of formula I or a pharmaceutically-acceptable salt of either of them to the animal. The invention also relates to a kit comprising a container holding a diketopiperazine of formula I, a prodrug of a diketopiperazine of formula I or a pharmaceutically-acceptable salt of either of them; and instructions for administration of the diketopiperazine, the prodrug or the pharmaceutically-acceptable salt according to a method of the invention.

BACKGROUND

Metabolic syndrome is a complex of risk factors for cardiovascular disease and type 2 diabetes. The most widely recognized of the risk factors are atherogenic dyslipidemia, elevated blood pressure and elevated plasma glucose. In addition, patients with these characteristics commonly manifest a prothrombotic state and a proinflammatory state. Atherogenic dyslipidemia consists of an aggregation of lipoprotein abnormalities that includes elevated serum triglyceride and apolipoprotein B, increased small low-density lipoprotein particles and a reduced level of high-density lipoprotein cholesterol. Most patients with metabolic syndrome also have abdominal (central) obesity and insulin resistance. For general background on metabolic syndrome factors and diagnosis, see Alberti et al., *Circulation*, 120:1640-1645 (2009).

Metabolic syndrome is common and has a rising prevalence worldwide, which relates largely to increasing obesity and sedentary lifestyles. Patients with the metabolic syndrome are at twice the risk of developing cardiovascular disease over the next five to ten years as individuals without the syndrome. The risk over a lifetime undoubtedly is even higher. Furthermore, the metabolic syndrome confers a five-fold increase in risk for type 2 diabetes mellitus. Metabolic syndrome is now both a public health and a clinical problem, and there is clearly a need for new and effective treatments for metabolic syndrome.

SUMMARY OF THE INVENTION

The invention provides such a treatment. In particular, the invention provides a method of treating metabolic syndrome in an animal. The method comprises administering to the animal an effective amount of an active ingredient, wherein the active ingredient comprises a diketopiperazine of formula I given below, a prodrug of a diketopiperazine of formula I or a pharmaceutically-acceptable salt of either of them.

The invention also provides a method of suppressing the appetite of an animal, a method of treating obesity in an animal, a method of reducing the weight of an animal in need thereof, a method of reducing a blood lipid level in an animal in need thereof, a method of treating non-alcoholic steatohepatitis in an animal, and a method of inhibiting adipogenesis in an animal. These methods also comprise administering an effective amount of an active ingredient, wherein the active ingredient comprises a diketopiperazine of formula I, a prodrug of a diketopiperazine of formula I or a pharmaceutically-acceptable salt of either of them to the animal.

The invention further provides a kit comprising a container holding a diketopiperazine of formula I, a prodrug of a diketopiperazine of formula I or a pharmaceutically-acceptable salt of either of them; and instructions for administration of the diketopiperazine, the prodrug or the pharmaceutically-acceptable salt according to a method of the invention.

The diketopiperazines useful in the invention have the following formula I:

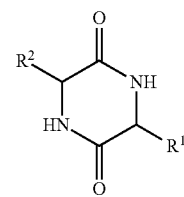

wherein:

$R^1$ and $R^2$, which may be the same or different, each is:

(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; or (b) $R^1$ is —$CH_2$—$CH_2$—$CH_2$— or —$CH_2$—CH(OH)—$CH_2$— and together with the adjacent ring nitrogen forms proline or hydroxyproline and/or $R^2$ is —$CH_2$—$CH_2$—$CH_2$— or —$CH_2$—CH(OH)—$CH_2$— and together with the adjacent ring nitrogen forms proline or hydroxyproline; or (b) a derivative of a side chain of an amino acid, wherein the amino acid is one of those recited in (a), and the derivatized side chain has:

(i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;

(ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;

(iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;

(iv) a —COOH group replaced by a —CON($R^4$)$_2$ group, wherein each $R^4$ may independently be H or a substituted or unsubstituted alkyl, cycloalkyl, heterocycloalkyl, aryl, alkylaryl, arylalkyl or heteroaryl;

(v) an —SH group replaced by —S—S—CH$_2$—CH(NH$_2$)—COOH or —S—S—CH$_2$—CH$_2$—CH(NH$_2$)—COOH;

(vi) a —CH$_2$— group replaced by a —CH(NH$_2$)— or a —CH(OH)— group;

(vii) a —CH$_3$ group replaced by a —CH$_2$—NH$_2$ or a —CH$_2$—OH group; and/or (viii) an H which is attached to a carbon atom replaced by a halogen;

provided, however, that when $R^1$ is the side chain of histidine or a derivative of the side chain of histidine, then $R^2$ cannot be proline or hydroxyproline, and that when $R^2$ is the side chain of histidine or a derivative of the side chain of histidine, then $R^1$ cannot be proline or hydroxyproline.

BRIEF DESCRIPTION OF THE DRAWING

FIG. 1: Effect of DA-DKP on adipogenesis. Statistical significance versus untreated controls is indicated by an asterisk (*).

DETAILED DESCRIPTION OF THE PRESENTLY-PREFERRED EMBODIMENTS OF THE INVENTION

The invention provides (i) a method of treating metabolic syndrome in an animal, (ii) a method of suppressing the appetite of an animal, (iii) a method of treating obesity in an animal, (iv) a method of reducing the weight of an animal in need thereof, such as an obese or overweight animal, (v) a method of reducing a blood lipid level in an animal in need thereof, and (vi) a method of treating non-alcoholic steatohepatitis in an animal.

The methods of the invention comprise administering an effective amount of an active ingredient, wherein the active ingredient comprises a diketopiperazine, a prodrug of a diketopiperazine or a pharmaceutically-acceptable salt of either of them to the animal, wherein the diketopiperazine has the following formula I:

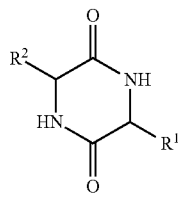

wherein:

$R^1$ and $R^2$, which may be the same or different, each is:

(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; or (b) $R^1$ is —CH$_2$—CH$_2$—CH$_2$— or —CH$_2$—CH(OH)—CH$_2$— and together with the adjacent ring nitrogen forms proline or hydroxyproline and/or $R^2$ is —CH$_2$—CH$_2$—CH$_2$— or —CH$_2$—CH(OH)—CH$_2$— and together with the adjacent ring nitrogen forms proline or hydroxyproline; or (b) a derivative of a side chain of an amino acid, wherein the amino acid is one of those recited in (a), and the derivatized side chain has:

(i) an —NH$_2$ group replaced by an —NHR$^3$ or —N(R$^3$)$_2$ group, wherein each $R^3$ may independently be a substituted or unsubstituted alkyl, cycloalkyl, heterocycloalkyl, aryl, alkylaryl, arylalkyl or heteroaryl;

(ii) an —OH group replaced by an —O—PO$_3$H$_2$ or —OR$^3$ group, wherein each $R^3$ may independently be a substituted or unsubstituted alkyl, cycloalkyl, heterocycloalkyl, aryl, alkylaryl, arylalkyl or heteroaryl;

(iii) a —COOH group replaced by a —COOR$^3$ group, wherein each $R^3$ may independently be a substituted or unsubstituted alkyl, cycloalkyl, heterocycloalkyl, aryl, alkylaryl, arylalkyl or heteroaryl;

(iv) a —COOH group replaced by a —CON($R^4$)$_2$ group, wherein each $R^4$ may independently be H or a substituted or unsubstituted alkyl, cycloalkyl, heterocycloalkyl, aryl, alkylaryl, arylalkyl or heteroaryl;

(v) an —SH group replaced by —S—S—CH$_2$—CH(NH$_2$)—COOH or —S—S—CH$_2$—CH$_2$—CH(NH$_2$)—COOH;

(vi) a —CH$_2$— group replaced by a —CH(NH$_2$)— or a —CH(OH)— group;

(vii) a —CH$_3$ group replaced by a —CH$_2$—NH$_2$ or a —CH$_2$—OH group; and/or (viii) an H which is attached to a carbon atom replaced by a halogen;

provided, however, that when $R^1$ is the side chain of histidine or a derivative of the side chain of histidine, then $R^2$ cannot be proline or hydroxyproline, and that when $R^2$ is the side chain of histidine or a derivative of the side chain of histidine, then $R^1$ cannot be proline or hydroxyproline.

By "replaced" is meant that, with reference to the formula of an amino acid side chain, the specified group is replaced by the other specified group. For instance, the formula of the isoleucine side chain is —CH(CH$_3$)—CH$_2$—CH$_3$. If the terminal —CH$_3$ group is replaced with a —CH$_2$—OH group, then the formula of the resulting derivatized isoleucine side chain would be —CH(CH$_3$)—CH$_2$—CH$_2$—OH. As another example, the formula of the alanine side chain is —CH$_3$. If one of the hydrogen atoms is replaced by a chlorine atom, then the resulting derivatized alanine side chain would be —CH$_2$—Cl. Note that the side chain of glycine is —H and, if this H is replaced by a chlorine (or other halogen) atom, the resulting side chain will —Cl, with the chlorine atom attached to the ring carbon (e.g., $R^1$=—Cl)

By "side chain" of an amino acid is meant that portion of the amino acid attached to the common

backbone of all of the amino acids listed above. For instance, the side chain of glycine is —H, the side chain of alanine is —CH$_3$, and the side chain of serine is —CH$_2$OH.

By "hydrophobic" is meant a side chain or side chain derivative that is uncharged at physiological pH and is repelled by an aqueous solution.

By "neutral" is meant a side chain or side chain derivative that is uncharged at physiological pH.

By "basic" is meant a side chain or side chain derivative that is positively charged at physiological pH.

By "acidic" is meant a side chain or side chain derivative that is negatively charged at physiological pH.

By "alkyl" is meant a saturated straight-chain or branched hydrocarbon containing 1-10 carbon atoms, preferably 1-6, carbon atoms. "Lower alkyl" means a saturated straight-chain or branched hydrocarbon containing 1-6 carbon atoms.

By "cycloalkyl" is meant a saturated cyclic hydrocarbon containing at least one ring, each ring containing at least three carbon atoms. Preferably, the cycloalkyl contains one ring of 4-8 carbon atoms.

By "heterocycloalkyl" is meant a cycloalkyl having one or more of the ring carbon atoms of at least one of the rings replaced by an O, S and/or N.

By "aryl" is meant an aromatic group having at least one aromatic ring (e.g., phenyl).

By "alkylaryl" is meant a lower alkyl having an H replaced by an aryl (e.g., —CH$_2$—C$_6$H$_5$ or —CH$_3$CH(C$_6$H$_5$)CH$_3$).

By "arylalkyl" is meant an aryl having an H replaced by a lower alkyl (e.g., —C$_6$H$_4$—CH$_3$).

By "heteroaryl" is meant an aryl having one or more of the ring carbon atoms of at least one of the rings replaced by an O, S and/or N.

By "substituted" is meant that the moiety is substituted with one or more substituents selected from the following group: —OH, NH$_2$, —SH, —COOH and/or a halogen atom.

By "halogen" is meant chlorine, fluorine, bromine or iodine. Preferred is chlorine or bromine.

Most preferred for use in the invention are diketopiperazines of formula I wherein R$^1$, R$^2$ or both is the side chain of aspartic acid or glutamic acid or a derivative of such a side chain wherein the —COOH group is replaced by a —COOR$^3$ group or a —CON(R$^4$)$_2$ group, wherein R$^3$ and R$^4$ are defined above. Of this group of compounds, preferred are diketopiperazines comprising the side chains of aspartic acid and alanine (Asp-Ala DKP or DA-DKP), the side chains of glutamic acid and alanine (Glu-Ala DKP or EA-DKP), the side chains of tyrosine and aspartic acid (Tyr-Asp DKP or YD-DKP), the side chains of tyrosine and glutamic acid (Tyr-Glu DKP or YE-DKP) and derivatives of the aspartic acid or glutamic acid side chains of these four diketopiperazines wherein the —COOH group is replaced by a —COOR$^3$ group or a —CON(R$^4$)$_2$ group, wherein R$^3$ and R$^4$ are defined above. Most preferred is DA-DKP.

Also preferred are diketopiperazines wherein R$^1$, R$^2$ or both are hydrophobic side chains or hydrophobic side chain derivatives. By "hydrophobic side chain derivative" is meant that the derivatized side chain is hydrophobic. In particular, preferred are diketopiperzines wherein R$^1$ and/or R$^2$, which may be the same or different, each is the side chain of glycine, alanine, valine, norvaline, α-aminobutyric acid, leucine, isoleucine, norleucine, methionine, phenylalanine, tryptophan or tyrosine. Of this group, preferred are diketopiperzines wherein R$^1$ and/or R$^2$, which may be the same or different, each is the side chain of glycine, alanine, valine, norvaline, α-aminobutyric acid, leucine, isoleucine, norleucine, methionine or tyrosine, more preferably alanine, valine, norvaline, α-aminobutyric acid, leucine, isoleucine or norleucine. Generally, proline is not preferred, although it is hydrophobic.

Additional preferred diketopiperazines are those wherein R$^1$, R$^2$ or both side chains are neutral side chains or neutral side chain derivatives. By "neutral side chain derivative" is meant that the derivatized side chain is neutral. In particular, preferred are diketopiperzines wherein R$^1$ and/or R$^2$, which may be the same or different, each is the side chain of asparagine, glutamine, serine, homoserine, threonine, tyrosine, cysteine or methionine. Of this group, preferred are diketopiperzines wherein R$^1$ and/or R$^2$, which may be the same or different, each is the side chain of asparagine, glutamine, serine or threonine.

Also preferred are diketopiperazines wherein R$^1$, R$^2$ or both are basic side chains or basic side chain derivatives. By "basic side chain derivative" is meant that the derivatized side chain is basic. In particular, preferred are diketopiperzines wherein R$^1$ and/or R$^2$, which may be the same or different, each is the side chain of citrulline, 2,4-diaminobutryic acid, 2,3-diaminobutyric acid, lysine, hydroxylysine, arginine, homoarginine, citrulline, p-aminophenylalanine, or ornithine. Of this group, preferred are diketopiperzines wherein R$^1$ and/or R$^2$, which may be the same or different, each is the side chain of citrulline, 2,4-diaminobutryic acid, 2,3-diaminobutyric acid, lysine, arginine, homoarginine or p-aminophenylalanine. Generally, histidine is not preferred, although it is basic.

Further preferred diketopiperazines are those wherein R$^1$, R$^2$ or both is the side chain of methionine, the side chain of arginine or a derivative of these side chains. Most preferred of this group is a diketopiperazine wherein R$^1$ is the side chain of methionine and R$^2$ is the side chain of arginine (Met-Arg DKP or MR-DKP).

Highly preferred for use herein is DA-DKP. Patients with metabolic syndrome can be treated by administering an effective amount of a DA-DKP, a prodrug of a DA-DKP or a pharmaceutically-acceptable salt of either of them. DA-DKP has multiple activities that should make it a particularly effective treatment for metabolic syndrome.

First, DA-DKP has been found to suppress the appetite. DA-DKP has also been found to inhibit the differentiation of preadipocytes into adipocytes. Accordingly, it is expected to be beneficial in the treatment of metabolic syndrome by contributing to weight loss and the treatment of obesity. It can also be used as a treatment for obesity and for weight loss in general, not just the obesity and excess weight associated with metabolic syndrome.

In addition, DA-DKP has also been found to reduce levels of lipids (cholesterol, triglycerides, low-density lipoprotein and high-density lipoprotein) in blood. For this reason, it is expected to have beneficial effects on the dyslipidemia which is one of the risk factors of metabolic syndrome.

Another pathological condition associated with the metabolic syndrome is the development of non-alcoholic steatohepatitis (NASH) in obese patients. NASH is characterized by an accumulation of lipid molecules in the liver accompanied by severe inflammation, fibrosis, and insulin/leptin resistance. In view of the foregoing activities of DA-DKP, it is expected to be beneficial in the treatment of NASH, whether associated with metabolic syndrome or independent of metabolic syndrome.

Further, DA-DKP has beneficial effects on the vascular endothelial barrier, including the ability to inhibit vascular hyperpermeability. Accordingly, it is expected to be an effective treatment for those exhibiting early signs of, or with a predisposition to, type 2 diabetes, such as those diagnosed with metabolic syndrome, to reduce, delay or even potentially prevent the vascular complications of diabetes. See Applicant's co-pending provisional application No. 61/380,404, filed Sep. 7, 2010.

Finally, DA-DKP is known to inhibit the aggregation of platelets, to be anti-inflammatory and to inhibit the activation of T-cells. See U.S. Pat. Nos. 6,555,543 and 7,732,403. Accordingly DA-DKP is expected to be useful in combating the prothrombotic and proinflammatory states observed in metabolic syndrome.

Methods of making diketopiperazines are well known in the art, and these methods may be employed to synthesize the diketopiperazines of the invention. See, e.g., U.S. Pat. Nos. 4,694,081, 5,817,751, 5,990,112, 5,932,579 and 6,555,543, US Patent Application Publication Number 2004/0024180, PCT applications WO 96/00391 and WO 97/48685, and Smith et al., *Bioorg. Med. Chem. Letters,* 8, 2369-2374 (1998), the complete disclosures of which are incorporated herein by reference.

For instance, diketopiperazines can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques.

For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determine by the person skilled in the art. It will advantageously be 2-9, preferably 3-7.

When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

To prepare diketopiperazines wherein the amino acid side chains are derivatized, amino acid derivatives can be used in the synthesis of the dipeptides, the dipeptides can be derivatized and/or the diketopiperazines can be derivatized, as is known in the art. See, e.g., those references cited above.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made from proteins and peptides as described in U.S. Pat. No. 7,732,403, the complete disclosure of which is incorporated herein by reference. Further, diketopiperazines for use in the practice of the invention can be obtained commercially from, e.g., Syngene, India and Hemmo Pharmaceuticals Pvt. Ltd, India (both custom synthesis).

The diketopiperazines of the invention include all possible stereoisomers than can be obtained by varying the configuration of the individual chiral centers, axes or surfaces. In other words, the diketopiperazines include all possible diastereomers, as well as all optical isomers (enantiomers).

"Prodrug" means any compound which releases an active parent drug (a diketopiperazine in this case) in vivo when such prodrug is administered to an animal. Prodrugs of diketopiperazines include derivatives that may be cleaved in vivo to generate the diketopiperazine. Examples of diketopiperazine prodrugs include esters.

The physiologically-acceptable salts of the diketopiperazines and prodrugs of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

As noted above, a diketopiperazine of formula I, a prodrug of a diketopiperazine of formula I or a pharmaceutically-acceptable salt of either one of them can be used in the methods of the invention. To do so, the diketopiperazine, prodrug or pharmaceutically-acceptable salt is administered to an animal in need of treatment. Preferably, the animal is a mammal, such as a rabbit, goat, dog, cat, horse or human. Most preferably, the animal is a human.

A diketopiperazine of formula I, a prodrug of a diketopiperazine of formula I or a pharmaceutically-acceptable salt of either one of them is used in the present invention as an active ingredient. "Active ingredient" is used herein to mean a compound having therapeutic, pharmaceutical or pharmacological activity, and particularly the therapeutic, pharmaceutical or pharmacological activities described herein. The diketopiperazine, prodrug or salt of either one of them is not used in the present invention as a carrier or as part of a carrier system of a pharmaceutical composition as described in, e.g., U.S. Pat. Nos. 5,976,569, 6,099,856, 7,276,534 and PCT applications WO 96/10396, WO 2006/023943, WO 2007/098500, WO 2007/121411 and WO 2010/102148.

Effective dosage forms, modes of administration and dosage amounts for the compounds of the invention (i.e., a diketopiperazine of formula I, a prodrug of a diketopiperazine of formula I or a pharmaceutically-acceptable salt of either one of them) may be determined empirically using the guidance provided herein. It is understood by those skilled in the art that the dosage amount will vary with the particular disease or condition to be treated, the severity of the disease or condition, the route(s) of administration, the duration of the treatment, the identity of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

In particular, an effective dosage amount of a diketopiperazine of formula I will be from 10 ng/kg/day to 225 mg/kg/day, preferably from 500 ng/kg/day to 150 mg/kg/day, most preferably from 1 mg/kg/day to 30 mg/kg/day. When given orally to an adult human, the dose will preferably be from about 1 mg/day to about 10 g/day, more preferably the dose will be from about 60 mg/day to about 6 g/day, most preferably the dose will be from about 100 mg/day to about 1200 mg/day, preferably given in several doses.

The compounds of the present invention (i.e., a diketopiperazine of formula I, prodrugs thereof and pharmaceutically-acceptable salts of either of them) may be administered to an animal patient for therapy by any suitable route of administration, including orally, nasally, parenterally (e.g., intravenously, intraperitoneally, subcutaneously or intramuscularly), transdermally, intraocularly and topically (including buccally and sublingually). Generally preferred is oral administration for any disease or condition treatable according to the invention.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., a diketopiperazine of formula I, a prodrug of a diketopiperazine of formula I, a pharmaceutically-acceptable salt of either one of them, or combinations of the foregoing) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The invention also provides pharmaceutical products suitable for treatment of the eye. Such pharmaceutical products include pharmaceutical compositions, devices and implants (which may be compositions or devices).

Pharmaceutical formulations (compositions) for intraocular injection of a compound or compounds of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, the complete disclosures of which are incorporated herein by reference. For instance, a pharmaceutical formulation for intraocular injection may comprise one or more compounds of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer). Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly(lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled.

The compounds of the invention can also be administered surgically as an ocular implant. For instance, a reservoir container having a diffusible wall of polyvinyl alcohol or polyvinyl acetate and containing a compound or compounds of the invention can be implanted in or on the sclera. As another example, a compound or compounds of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anesthetic and using a small incision made behind the cornea. The matrix is then inserted through the incision and sutured to the sclera.

The compounds of the invention can also be administered topically to the eye, and a preferred embodiment of the invention is a topical pharmaceutical composition suitable for application to the eye. Topical pharmaceutical compositions suitable for application to the eye include solutions, suspensions, dispersions, drops, gels, hydrogels and ointments. See, e.g., U.S. Pat. No. 5,407,926 and PCT applications WO 2004/058289, WO 01/30337 and WO 01/68053, the complete disclosures of all of which are incorporated herein by reference.

Topical formulations suitable for application to the eye comprise one or more compounds of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye will preferably comprise an absorption or permeation enhancer to promote absorption or permeation of the compound or compounds of the invention into the eye and/or a thickening agent or viscosity enhancer that is capable of increasing the residence time of a compound or compounds of the invention in the eye. See PCT applications WO 2004/058289, WO 01/30337 and WO 01/68053. Exemplary absorption/permeation enhancers include methysulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) suitable for treatment of the eye can be prepared, for example, by dissolving, dispersing, suspending, etc. a compound or compounds of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxillary substances, such as wetting or emulsifying agents, pH buffering agents and the like, for example sodium acetate, sorbitan monolaurate, triethanolamine sodium acetate, triethanolamine oleate, etc.

Aqueous solutions and suspensions suitable for treatment of the eye can include, in addition to a compound or compounds of the invention, preservatives, surfactants, buffers, salts (preferably sodium chloride), tonicity agents and water. If suspensions are used, the particle sizes should be less than 10 μm to minimize eye irritation. If solutions or suspensions are used, the amount delivered to the eye should not exceed 50 μl to avoid excessive spillage from the eye.

Colloidal suspensions suitable for treatment of the eye are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5μ, to about 10μ.

Ophthalmic ointments suitable for treatment of the eye include a compound or compounds of the invention in an appropriate base, such as mineral oil, liquid lanolin, white petrolatum, a combination of two or all three of the foregoing, or polyethylene-mineral oil gel. A preservative may optionally be included.

Ophthalmic gels suitable for treatment of the eye include a compound or compounds of the invention suspended in a hydrophilic base, such as Carpobol-940 or a combination of ethanol, water and propylene glycol (e.g., in a ratio of 40:40:20). A gelling agent, such as hydroxyethylcellulose, hydroxypropylcellulose, hydroxypropylmethylcellulose or ammoniated glycyrrhizinate, is used. A preservative and/or a tonicity agent may optionally be included.

Hydrogels suitable for treatment of the eye are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the Pluronic® tradename from BASF-Wayndotte).

Preferred dispersions are liposomal, in which case the formulation is enclosed within liposomes (microscopic vesicles composed of alternating aqueous compartments and lipid bilayers).

Eye drops can be formulated with an aqueous or nonaqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The compounds of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired compound of the invention, as well as biodegradable or soluble devices that need not be removed after placement in the eye. These soluble ocular inserts can be composed of any degradable substance that can be tolerated by the eye and that is compatible with the compound of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

Dosage forms for the other types of topical administration (i.e., not to the eye) or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. A drug-impregnated solid carrier (e.g., a dressing) can also be used for topical administration.

Pharmaceutical formulations include those suitable for administration by inhalation or insufflation or for nasal administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents. Also, drug-coated stents may be used.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multidose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

A diketopiperazine of formula I, a prodrug of a diketopiperazine of formula I or a pharmaceutically-acceptable salt of either one of them, may be given alone in the methods of the invention. Alternatively, the diketopiperazine, prodrug or salt may be given in combination with each other and/or in combination with one or more other treatments or drugs suitable for treating the disease or condition. For instance, the diketopiperazine, the prodrug or the salt can be administered prior to, in conjunction with (including simultaneously with), or after another treatment or drug. In the case of another drug, the drug and the diketopiperazine, prodrug or salt, may be administered in separate pharmaceutical compositions or as part of the same pharmaceutical composition.

The invention also provides kits. The kit comprises a container holding a diketopiperazine of formula I, a prodrug thereof or a pharmaceutically-acceptable salt of either of them. The kit may further comprise one or more additional containers each holding one or more other drugs suitable for use in the methods of the invention. Suitable containers include vials, bottles (including a bottle with a dropper or a squeeze bottle), blister packs, inhalers, jars, nebulizers, packets (e.g., made of foil, plastic, paper, cellophane or another material), syringes and tubes. The kit will also contain instructions for administration of the diketopiperazine, prodrug or salt and, optionally, the one or more other drugs suitable for use in the methods of the invention. The instructions may, for instance, be printed on the packaging holding the container(s), may be printed on a label attached to the kit or the container(s), or may be printed on a separate sheet of paper that is included in or with the kit. The packaging holding the container(s) may be, for instance, a box, or the container(s) may wrapped in, for instance, plastic shrink wrap. The kit may also contain other materials which are known in the art and which may be desirable from a commercial and user standpoint. The kit may, for instance, contain diet and/or exercise information.

As used herein, "obese" or "obesity" means a medical condition in which excess body fat has accumulated to the extent that it may have an adverse effect on health, leading to reduced life expectancy and/or increased health problems. Obesity increases the likelihood of various diseases, particularly heart disease, type 2 diabetes, breathing difficulties during sleep, certain types of cancer and osteoarthritis. According to the Centers For Disease Control And Prevention (CDC), a body mass index (BMI) of 30 or higher defines adult humans as obese, and a BMI of from 25.0 to 29.9 defines adult humans as overweight. BMI is calculated by dividing the subject's mass by the square of his or her height (e.g., (pounds×703)/inches$^2$). "Obesity" in cats and dogs is defined as a body weight that is greater than 20% above optimal body weight.

"Treat," "treating" or "treatment" is used herein to mean to reduce (wholly or partially) the symptoms, duration or severity of a disease or condition, including curing the disease, or to prevent the disease or condition.

"Inhibiting, "inhibit" and similar terms are used herein to mean to reduce, delay or prevent.

As used herein, "a" or "an" means one or more.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein. The basic and novel characteristics of the invention can be treatment of metabolic syndrome, suppression of the appetite of an animal in need thereof, treatment of obesity in an animal, reduction of the weight of an animal in need thereof, reduction of a blood lipid level in an animal in need thereof, treatment of non-alcoholic steatohepatitis in an animal, inhibition of adipogenesis in an animal, or a combination of any of the foregoing.

Additional objects, advantages and novel features of the present invention will become apparent to those skilled in the art by consideration of the following non-limiting examples.

EXAMPLES

Example 1

Protocol

1. Two human male volunteers and one human female volunteer (ages 61, 50 and 30 respectively) were administered 100 mg of DA-DKP (packed in a gelatin capsule) orally on an empty stomach after overnight fasting. The DA-DKP was composed of L-aspartic acid and L-alanine.

2. Venous blood samples were drawn into heparinized and EDTA vacutainers at baseline (time zero), 2 hours (hrs), 4 hrs and 24 hrs after the ingestion of the DA-DKP.
3. Blood samples were analyzed for a complete blood count (CBC) and a biochemical survey, including plasma lipids at baseline and at the 24 hrs time points. Plasma was also used for measurement of the level of DA-DKP by a liquid chromatography mass spectrometer (LCMS) method (protocol and results given below).
4. Peripheral blood monocytes (PBMC) from heparinized bloods were extracted by Ficoll gradient method and analyzed by flow cytometry. The protocol and results are given below.
5. Urines were collected for 24 hrs and volumes were recorded. DA-DKP levels were also measured by LCMS.
6. Saliva at 2 hrs was tested for the presence of DA-DKP by LCMS.

Summary of Results:
1. CBC's were unchanged and remained within the normal range.
2. BUN, glucose electrolytes, creatinine, liver function tests, total protein, albumin and calcium were unchanged and within the normal range at 24 hours post ingestion.
3. Lipids decreased across the board for all three subjects at 24 hours post ingestion (see Table 1).
4. DA-DKP plasma levels peaked at about 2 hrs and it was not detectable at 24 hrs post ingestion (see Table 2).
5. Urine levels of DA-DKP were calculated (see Table 2).
6. Saliva DA-DKP levels were calculated (see Table 2)
7. PBMC results are described below.
8. Effects noticed by subjects:
    a. Significant loss of appetite (lasting 8-9 hrs)—3/3 subjects
    b. Slight dry mouth—2/3 subjects
    c. Thick saliva—1/3 subjects
    d. Analgesic effect—1/3 subjects (others did not have pain)*
    e. Laxative effect—1/3 subjects
    f. Slight drowsiness—1/3 subjects

* Analgesic Effect:
One subject (61 years old) had left knee and left Sacroiliac (SI) joint pain. Approximately 1-2 hrs after ingestion of the DA-DKP, the knee pain was resolved completely and the SI joint pain was reduced by about 50%. The pain originates probably from inflammation caused by sarcoidosis and was 6-7 on a scale of 1-10 before treatment. The effect lasted for about 4 hrs.

TABLE 1

| (% Change in Lipids after 24 Hours) | | | | |
|---|---|---|---|---|
| | Cholesterol | LDL | HDL | Triglyceride |
| 1 (61 years) | −9.2% | −10% | −12% | −2.1% |
| 2 (30 years) | −3.0% | −7.9% | −7% | +0.5% |
| 3 (50 years)* | −1.3% | −6.6% | −6.7% | +28.1% (had large fatty meal the night before) |

*The 50 year-old male has Gilbert disease

DA-DKP LCMS Measurement

Plasma or urines were passed through a <5 Kd filter and 50 μl of the flow-through fractions were injected into high performance liquid chromatography (HPLC, 2975 system, Waters, Mass.) coupled to a mass spectrometer (LCT-TOF, Micromass, UK) and DA-DKP was quantified using a strong anion exchange column (Spherisorb, S5 SAX 250 mm×4.0 mm, Waters) and a ternary mobile phase consisting of water, methanol and 200 mM Ammonium Formate (Sigma Aldrich, Mo.), pH 5.4, at 0.5 ml/min flow rate in a gradient as shown in Table A.

TABLE A

| Time (min) | Water (%) | Methanol (%) | 200 mM Ammonium Formate pH 5.4 (%) |
|---|---|---|---|
| 0 | 25 | 40 | 35 |
| 10 | 10 | 40 | 50 |
| 15 | 10 | 40 | 50 |
| 15.01 | 25 | 40 | 35 |
| 20 | 25 | 40 | 35 |

The output of the HPLC was split 1:20 (v:v) and injected into the mass spectrometer using negative electrospray ionization (−ESI MS) with a scan range of 80 to 1000 m/z, cone voltage of 30 eV, source temperature of 100° C., and gas temperature of 300° C. DA-DKP was measured by monitoring the mass 185 in time, which corresponds to DA-DKP minus a single proton (—H+). DA-DKP elutes at 10.4 minutes and was quantified by integrating the area under the curve. The area was compared to a standard curve derived from synthetic DA-DKP standards (DMI Synthesis, Newport Wales, UK) of known concentrations (2000 ng/ml, 1000 ng/ml, 400 ng/ml, 200 ng/ml, 100 ng/ml, 20 ng/ml). The calibration curve was found to fit very well in this range using a quadratic curve on log axes with an $R^2$ of 0.997.

The results are presented in Table 2 below. The results are for plasma unless otherwise noted in Table 2.

TABLE 2

| | (DA-DKP in μM) | | | | | | | | |
|---|---|---|---|---|---|---|---|---|---|
| | 0 | 15 min | 30 min | 60 min | 120 min | 240 min | 360 min | 24 hrs | Urine 24 hrs | Saliva 2 hrs |
| 1 (61 years old) | 0 | 0.14 | 0.35 | 0.84 | 1.68 | NA | 0.61 | 0.25 | 6.98 (2150 cc) | NA |
| 2 (30 years old) | 0.07 | NA | NA | NA | 0.4 | 0.34 | NA | 0.14 | 3.52 (3500 cc) | 0.29 |
| 3 (50 years old) | 0.1 | NA | NA | NA | 0.54 | 0.25 | NA | 0.09 | 4.25 (2000 cc) | 0.22 |

PBMC Protocol and Results

Peripheral blood mononuclear cells (PBMC) were isolated from peripheral blood, and 2,000,000 cells were cultured in DMEM medium with 10% human AB serum plus 2% (final concentration) of anti-T-cell receptor complex antibody OKT3. A separate culture without OKT3 antibody was used as the NIL control. After culture overnight at 37° C. cells were washed, incubated with an anti-CD69 antibody, fixed and analyzed on the flow cytometer for CD69 expression. CD69 is an early activation antigen indicative of leukocyte immunocompetence. Results (for a single individual) indicated that CD69 expression on CD45RA and CD45RO cells was decreased after ingestion of DA-DKP from that before DA-DKP intake (time zero) with the greatest effect seen at 4 hours after DA-DKP ingestion. Dual histogram analysis indicated that the major effect was seen on the CD45RO (or previously activated "memory") subset of T-cells (4 hours, OKT3 Stim. panel).

Discussion

The main effects observed after oral administration of DA-DKP were the lack of appetite (which could lead to weight loss, obesity being a cardinal feature of the metabolic syndrome) and the decrease in blood cholesterol, triglycerides, LDL and HDL (dyslipidemia being another feature of the metabolic syndrome). Also, the prevention of activation of previously activated T cells in response to an anti-CD3 stimulation, but not of the naïve T cells, is an important finding (inflammation being implicated in the metabolic syndrome). These together with in vitro data showing the inhibition of the differentiation of preadipocytes into adipocytes by DA-DKP (see Example 2) and the beneficial effects of DA-DKP on the vascular endothelial barrier (see co-pending provisional application No. 61/380,404, filed Sep. 7, 2010), support the idea of using DA-DKP as a therapeutic for the metabolic syndrome.

Example 2

A. Introduction

Adipogenesis is a multi-step process that involves the conversion of stem cells into fat-storing cells termed adipocytes. Adipose tissue mass enlarges and ultimately obesity ensues when energy intake chronically exceeds energy expenditure (1) (the numbers in parentheses refer to the references listed at the end of this Example 2). At the cellular level, this balance shift manifests itself through mature adipocytes accommodating excess energy through enhanced triacylglycerol storage (2). When a critical size threshold is reached, it is hypothesized that overloaded adipocytes signal preadipocytes to differentiate into new adipocytes to store the excess energy (3). Not surprisingly, obese animals have an increased amount of, and larger, adipocytes compared with lean animals (4). Any factor that inhibits cellular differentiation into the adipocyte lineage could be medically useful in treating obesity. However, a complete understanding of the adipogenic pathway, both inhibitory and stimulatory pathways, is necessary since the modulation of adipose tissue mass may have both advantageous and deleterious health effects (5).

Recently, due to increased obesity research, adipose tissue is now recognized as an endocrine organ due to its hormonal role in the regulation of metabolism, energy intake, and fat storage (6). Adipose tissue accomplishes fat regulation by secreting >50 proteins, termed adipokines, that act in an autocrine, paracrine, and endocrine fashion to control various metabolic functions (6). The most studied adipokines are adiponectin and leptin which decrease serum free fatty acid, glucose, and triacylglycerol concentrations by insulin sensitivity enhancement (7), and influence food intake by the hypothalamus (8), respectively. Additionally, pro-inflammatory cytokines such as TNFα and IL-6 play an important role in normal and pathological adipogenesis (2). After receptor binding by adipokines and/or cytokines, various intercellular molecular pathways important to adipogenesis can become activated or inhibited. Activation of mitogen activated protein kinases (MAPK) has an important role in adipocyte differentiation, and deregulation of MAPK can contribute to obesity (9).

B. Materials and Methods

Cell Culture

Subcutaneous preadipocytes (Zen-Bio, Inc., Research Triangle Park, N.C.) were cultured to near confluency at 5% $CO_2$, 37° C. in Preadipocyte Growth Medium-2 (PGM-2, Lonza, Walkersville, Md.) containing 10% fetal bovine serum (FBS), L-glutamine, and GA-1000. Cells were harvested using trypsin/EDTA (Lonza) and initially seeded in 96-well black/clear bottom plates at 3,000 cells/well. Cells were allowed to form a confluent monolayer for 7 days in culture.

Cell Dosing and Differentiation 7-day old medium was aspirated and cells were dosed with DA-DKP (doses used in PGM-2 media: 25, 50, or 100 μM) in triplicate on two plates. The DA-DKP was composed of L-aspartic acid and L-alanine. PGM-2 differentiation media (containing insulin, dexamethasone, indomethacin, and isobutylmethylxanthine; Lonza) was added to one plate, while PGM-2 media was added to the other. Plates were then placed back in culture and allowed to incubate for 14 days.

Adipogenesis Assay

After the 14 day incubation period, culture media were collected from all wells and stored at −20° C. for IL-6 ELISA (see below). Wells were rinsed once with 1×PBS (Lonza). 50 μL M-PER lysis solution (Thermo Scientific, Rockford, Ill.) were added to all wells, and complete cell lysis was achieved by mixing each well. 150 μL 1×PBS was added to each well. 5 μL AdipoRed™ Reagent (Lonza) was added to each well, and the plate was mixed immediately by gentle tapping. After 10 minutes, fluorescence was measured on a plate reader set at $\lambda_{EX}$=485 nm and $\lambda_{EM}$=572 nm.

IL-6 ELISA

Enzyme-linked immunosorbent assay (ELISA) matched-pair antibodies for interleukin-6 (IL-6) were obtained from Thermo Scientific (Rockford, Ill.). IL-6 was analyzed by ELISA and performed according to the manufacturer's instructions. A 1:10 dilution of each supernatant was measured in duplicate using an IL-6 standard (Thermo Scientific, Rockford, Ill.).

Data Analysis

The triplicate fluorescent values for each treatment were averaged and subtracted from the average media only (i.e. no cells) wells. For the differentiated wells, a % change was calculated by subtracting the average fluorescent value for the differentiated cells from the undifferentiated cells for each treatment group. This result was then subtracted from the difference between the differentiated and undifferentiated control groups (i.e. cells only with no treatment). Finally, this result was then divided by the difference between the differentiated and undifferentiated control groups to give a % change. All data are expressed as ±SD. Statistical significance is reported when $p<0.05$ based on the Student t-test (Microsoft Excel).

C. Results

DA-DKP caused an increase in adipogenesis at the highest dose (100 μM) while the lowest dose (25 μM) caused a significant decrease in adipogenesis (see FIG. 1). Interestingly, DA-DKP had no significant effect on IL-6 levels after the 2 week differentiation period (data not shown).

D. Discussion

Obesity has been described as the epidemic of the 21$^{st}$ century due to an increase in the prevalence of obesity as well as an earlier age of onset (6). This results in a major public health issue since obesity increases the risk of several chronic diseases such as diabetes, cardiovascular complications, arthritis, asthma, and certain cancers (10). Naturally, the search for a therapeutic agent that reverses the deleterious effects of obesity is the subject of a considerable amount of current research efforts. In this study, DA-DKP was effective at preventing adipogenesis (as measured by total intracellular triglyceride concentrations).

A potential cellular pathway target of DA-DKP is the family of mitogen activated protein kinases (MAPK). MAPK are serine/threonine kinase that include extracellular signal-regulated kinases (ERK), c-Jun amino-terminal kinases (JNK), and p38. MAPKs are important in regulating both normal and pathological adipogenesis (9). Previously, the inhibitory effect of DA-DKP on MAPK activity in T-lymphocytes has been shown (12). It is possible that DA-DKP inhibits adipogenesis by MAPK inhibition, but specific inhibition of MAPK isoforms such as ERK1 and JNK1 seems promising in preventing pathological adipogenesis without interference to other essential MAPK functions (9).

Another important pathway involved in cellular differentiation including adipogenesis involves the cytoskeleton. Disruption of the actin cytoskeleton, forced cell rounding, microtubule disruption, and stress fiber formation are all observed cytoskeletal changes during adipogenesis (11). DA-DKP has been shown to stabilize the cytoskeletal network in endothelial cells (see co-pending provisional application No. 61/380, 404, filed Sep. 7, 2010).

DA-DKP is a naturally occurring molecule produced by an unknown mechanism involving the cleavage of the first two amino acids of human serum albumin and subsequent cyclization of the cleaved dipeptide (13). Additionally, DA-DKP has strong anti-inflammatory characteristics in immune cell models (12, 13). Interestingly, the pro-inflammatory pathway plays an important role in adipogenesis (6). In deregulated adipose tissue seen in obesity and diabetes, both local and systemic inflammation as well as insulin resistance and ectopic lipid accumulation are observed (14). Therefore, the anti-inflammatory tendencies of DA-DKP could be useful in combating the degree of inflammation seen in obese patients. However, no effect of DA-DKP on IL-6 levels was seen at the end of the differentiation period, suggesting that DA-DKP does not interfere with the pathway that regulates IL-6 levels during adipogenesis. This does not rule out the possibility of using DA-DKP as an anti-inflammatory in already obese patients.

Recently, a clustering of cardiovascular risk factors that include diabetes, obesity, dyslipidemia, and hypertension have been grouped together and termed the metabolic syndrome (15). It has been estimated that adults with the metabolic syndrome are twice as likely to develop cardiovascular disease compared to those without the syndrome (16). Clearly, decreases in abdominal obesity lead to substantial improvements in the metabolic risk profile resulting in a reduced risk of cardiovascular disease (17). Another pathological condition associated with the metabolic syndrome is the development of non-alcoholic steatohepatitis (NASH) in obese patients. NASH is characterized by an accumulation of lipid molecules in the liver accompanied by severe inflammation, fibrosis, and insulin/leptin resistance (18). Therefore, therapeutics that regulate further adipogenesis and/or decrease inflammation in adipose tissue could decrease the increased cardiovascular risk associated with the metabolic syndrome and be an effective treatment for NASH.

The increased prevalence of obesity in Western countries has lead to increases in various co-morbidities such as cardiovascular disease, hypertension, and diabetes. Searching for a therapeutic that increases fat metabolism and/or decreases fat storage has been the goal of many nutritional scientists. Here, evidence is presented of the anti-adipogenic effects of a compound that potentially targets a key regulator of adipogenesis (MAPK), stabilizes the cytoskeleton, and decreases inflammation, making it an attractive potential treatment for metabolic syndrome and a treatment to reduce obesity.

E. References for Example 2

1. Spiegelman B M, Flier J S. Obesity and the regulation of energy balance. *Cell* 2001; 104:531-543.
2. Harp J B. New insights into inhibitors of adipogenesis. *Curr Opin Lipidol* 2004; 15:303-307.
3. Prins J B, O'Rahilly S. Regulation of adipose cell number in man. *Clin Sci* (Lond) 1997; 92:3-11.
4. DiGirolamo M, Fine J B, Tagra K, et al. Qualitative regional differences in adipose tissue growth and cellularity in male Wistar rats fed ad libitum. *Am J Physiol* 1998; 274:R1460-1467.
5. Kahn B B, Flier J S. Obesity and insulin resistance. *J Clin Invest* 2000; 106:473-481.
6. Greenberg A S, Obin M S. Obesity and the role of adipose tissue in inflammation and metabolism. *Am J Clin Nutr* 2006; 83:461 S-465S.
7. Fruebis J, Tsao T S, Javorschi S, et al. Proteolytic cleavage product of 30-kDa adipocyte complement-related protein increases fatty acid oxidation in muscle and causes weight loss in mice. *Proc Natl Acad Sci USA* 2001; 98:2005-2010.
8. Lee G H, Proenca R, Montez J M, et al. Abnormal splicing of the leptin receptor in diabetic mice. *Nature* 1996; 379: 632-635.
9. Bost F, Aouadi M, Caron L, et al. The role of MAPKs in adipocyte differentiation and obesity. *Biochimie* 2005; 87:51-56.
10. Mokdad A H, Ford E S, Bowman B A, et al. Prevalence of obesity, diabetes, and obesity-related health risk factors, 2001. *Jama* 2003; 289:76-79.
11. Feng T, Szabo E, Dziak E, et al. Cytoskeletal disassembly and cell rounding promotes adipogenesis from ES cells. *Stem Cell Rev* 2010; 6:74-85.
12. Shimonkevitz R, Thomas G, Slone D S, et al. A diketopiperazine fragment of human serum albumin modulates T-lymphocyte cytokine production through rap 1. *J Trauma* 2008; 64:35-41.
13. Bar-Or D, Thomas G W, Bar-Or R, et al. Commercial human albumin preparations for clinical use are immunosuppressive in vitro. *Crit Care Med* 2006; 34:1707-1712.
14. Gustafson B, Smith U. Cytokines promote Wnt signaling and inflammation and impair the normal differentiation and lipid accumulation in 3T3-L1 preadipocytes. *J Biol Chem* 2006; 281:9507-9516.
15. Duvnjak L, Duvnjak M. The metabolic syndrome—an ongoing story. *J Physiol Pharmacol* 2009; 60 Suppl 7:19-24.
16. Grundy S M. Metabolic syndrome pandemic. *Arterioscler Thromb Vasc Biol* 2008; 28:629-636.

17. Despres J P. Is visceral obesity the cause of the metabolic syndrome? *Ann Med* 2006; 38:52-63.
18. Larter C Z, Chitturi S, Heydet D, et al. A fresh look at NASH pathogenesis. Part 1: the metabolic movers. *J Gastroenterol Hepatol* 2010; 25:672-690.

What is claimed:

1. A method of treating non-alcoholic steatohepatitis in an animal comprising administering to the animal in need thereof an effective amount of an active ingredient, wherein the active ingredient comprises a diketopiperazine, a prodrug of a diketopiperazine or a pharmaceutically-acceptable salt of either of them, wherein the diketopiperazine has the formula:

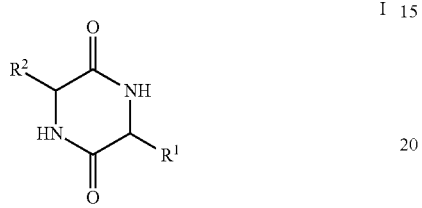

I wherein:
$R^1$ is the side chain of aspartic acid, and $R^2$ is the side chain of alanine.

2. The method of claim 1 wherein the diketopiperazine, prodrug or pharmaceutically-acceptable salt is administered orally.

3. The method of claim 1 wherein the animal is a human.

* * * * *